(12) United States Patent
Irie

(10) Patent No.: US 7,057,054 B2
(45) Date of Patent: Jun. 6, 2006

(54) PHOTOCHROMIC MATERIAL

(75) Inventor: Masahiro Irie, Fukuoka (JP)

(73) Assignee: Japan Science and Technology Corporation, Kawaguchi (JP)

( * ) Notice: Subject to any disclaimer, the term of this patent is extended or adjusted under 35 U.S.C. 154(b) by 41 days.

(21) Appl. No.: 10/649,868

(22) Filed: Aug. 28, 2003

(65) Prior Publication Data

US 2004/0049040 A1 Mar. 11, 2004

Related U.S. Application Data

(63) Continuation of application No. PCT/JP02/01946, filed on Mar. 4, 2002.

(30) Foreign Application Priority Data

Mar. 5, 2001 (JP) .............................. 2001-060382

(51) Int. Cl.
  *C07D 409/00* (2006.01)
  *C07F 2/00* (2006.01)
  *C08G 75/00* (2006.01)
(52) U.S. Cl. ..................... 549/59; 526/204; 528/380
(58) Field of Classification Search ............... 549/59; 526/204; 528/380
See application file for complete search history.

(56) References Cited

U.S. PATENT DOCUMENTS

| 5,734,065 A | * | 3/1998 | Saika ........................ 549/59 |
| 6,359,150 B1 | * | 3/2002 | Fukudome et al. .......... 549/59 |
| 6,479,604 B1 | * | 11/2002 | Kim et al. ................. 526/242 |
| 6,787,621 B1 | * | 9/2004 | Kim et al. ................. 526/204 |

FOREIGN PATENT DOCUMENTS

| EP | 1 405 891 | 4/2004 |
| JP | 2000-256664 | 9/2000 |
| JP | 2000-256665 | 9/2000 |
| JP | 2000-321714 | 11/2000 |
| JP | 2001-48875 | 2/2001 |
| JP | 2001-49244 | 2/2001 |

OTHER PUBLICATIONS

Chem Ab, 134: 186014, Ogura et al, 2001.*
Chem Ab, 131: 235806, Masahiro, Irie, 1999.*
Chemistry Letters 2001, vol. 7, Jul. 5, 201, Katsunori Shibata et al, pp. 618-619t Ricoh Co., Ltd.
K. Morimitsu et al: "Dithienylethenes with a Novel Photochromic Performance" Journal of Organic Chemistry, vol. 67, No. 13, 2002, pp. 4574-4578, XP002312626.

* cited by examiner

*Primary Examiner*—Deborah C. Lambkin
(74) *Attorney, Agent, or Firm*—Manabu Kanesaka

(57) ABSTRACT

A photochromic material having a ring opening quantum yield of $10^{-3}$ or lower which does not fade under ambient light is provided. The material comprises a compound belonging to the diheteroarylethene class. The compound has alkoxy group and aryl group on the heteroaryl group.

9 Claims, No Drawings

PHOTOCHROMIC MATERIAL

CROSS REFERENCE TO RELATED APPLICATION

This is a continuation application of PCT/JP02/01946 filed on Mar. 4, 2002.

FIELD OF THE INVENTION

The present invention relates to a photochromic material comprising a compound belonging to the diheteroarylethene class.

BACKGROUND OF THE INVENTION

Photochromic material includes molecules or molecule aggregates which can reversibly take the forms of two isomers having different states by photoisomerization. The photochromic material can be utilized as photonics materials such as optical memory media and optical display materials, because the photochromic material can change not only its color but also its various other physical properties—such as refractive index, dielectric constant, and oxidation/reduction potential under irradiation of light.

Japanese Unexamined Patent Publication No. H3-261782 discloses a photochromic material belonging to the diheteroarylethane class, having methoxy groups at two reactive positions participating in ring closing/ring opening reactions, as expressed by the following formula:

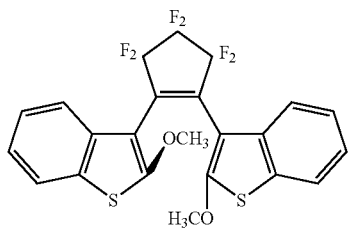

The record or image of the optical memory medium or optical display material of the photochromic material may disappear under ambient light such as a room light. When the quantum yield of ring opening reaction (hereinafter, referred to as "ring opening quantum yield") of a compound, belonging to the diarylethene class, in the closed-ring form is in the order of $10^{-2}$, the record or image will disappear almost completely in several hours under fluorescent room light.

The aforementioned compound belonging to the diheteroarylethene class disclosed in Japanese Unexamined Patent Publication No. H3-261782 has a ring opening quantum yield of $3.3 \times 10^{-2}$, which is larger than $10^{-2}$.

DISCLOSURE OF THE INVENTION

A photochromic material of the present invention comprises a compound, belonging to the diheteroarylethene class, represented by the following general formula [I]:

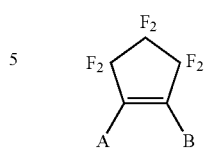

[I]

In the general formula [I], A represents substituents [i] or [ii] shown below, and B represents substituents [iii] or [iv] shown below.

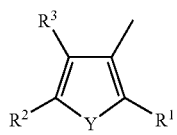

[i]

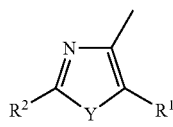

[ii]

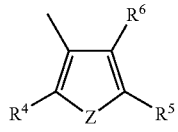

[iii]

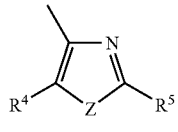

[iv]

In the substituents [i] and [ii], $R^1$ represents an alkoxy group, and $R^2$ represents -Q-Ar. Q represents a direct bond or an arbitrary divalent group, and Ar represents an aromatic hydrocarbon ring or an aromatic heterocycle, which are optionally substituted. $R^3$ represents a hydrogen atom, an alkyl group, an alkoxy group, a halogen atom, a fluoroalkyl group, a cyano group, or an aryl group which is optionally substituted, and Y represents —O— or —S—.

In the substituents [iii] and [iv], $R^4$ represents an alkoxy group, and $R^5$ represents -Q-Ar. Q represents a direct bond or an arbitrary divalent group, and Ar represents an aromatic hydrocarbon ring or an aromatic heterocycle, which are optionally substituted. $R^6$ represents a hydrogen atom, an alkyl group, an alkoxy group, a halogen atom, a fluoroalkyl group, a cyano group, or an aryl group which is optionally substituted, and Z represents —O— or —S—.

The photochromic material of the present invention has a ring opening quantum yield of $10^{-3}$ or lower.

DESCRIPTION OF THE PREFERRED EMBODIMENTS

Hereinafter, the present invention will be described in detai.

A photochromic material of the present invention comprises a compound, belonging to the diheteroarylethene class, represented by the abovementioned general formula [I].

In the substituents [i]–[iv] of the general formula [I], $R^1$ and $R^4$ each represent independently alkoxy group with 1–3 carbon atoms such as methoxy group and ethoxy group, preferably a methoxy group or an ethoxy group, more preferably a methoxy group.

$R^2$ and $R^5$ each represent independently -Q-Ar. Q represents a direct bond or an arbitrary divalent group, and Ar represents an aromatic hydrocarbon ring or an aromatic heterocycle, which are optionally substituted. In preferable structures, a conjugated system extends from both heteroaryl rings of the diarylethene structure to substituents $R^2$ and $R^5$. In the general formula [I], Q preferably comprises a direct bond, —(—CH═CH—)$_n$— (i.e. a polyethylene group) (wherein n 1–5), or —(—C"C—)$_n$— (i.e. a polyacetylene group) (wherein n=1–5), and Ar preferably comprises a group consisting of 5- or 6-member ring or a group consisting of two or three 5- or 6-member rings bonded directly or condensed, each of the groups being optionally substituted. When Ar has a substituent, the substituent includes a linear or branched alkyl group with 1–10 carbon atoms such as methyl group, ethyl group, butyl group, and hexyl group; a linear or branched alkoxy group with 1–10 carbon atoms such as methoxy group, ethoxy group, butoxy group, and hexyloxy group; a halogen atom such as fluorine atom and chlorine atom; and linear or branched fluoroalkyl group with 1–6 carbon atoms such as trifluoromethyl group, pentafluoroethyl group, 2-fluoroethyl group, 2,2-difluoroethyl group, perfluoro-n-hexyl group, and 2-(perfluorobutyl) ethyl group.

In a diarylethene structure, it is preferable that the heteroaryl rings (the heterocycles comprising —Y— or -Z-, shown in structures [i]–[iv]) and $R^2$ or $R^5$ form a same plane. For this purpose, it is preferable that the diarylethene structure represented by the general formula [I] has a relatively low-volumed group at the ortho-position of Ar (ortho-position relative to the position at which Ar is bonded to heteroaryl ring)

Specific examples of Ar include the following formulae:

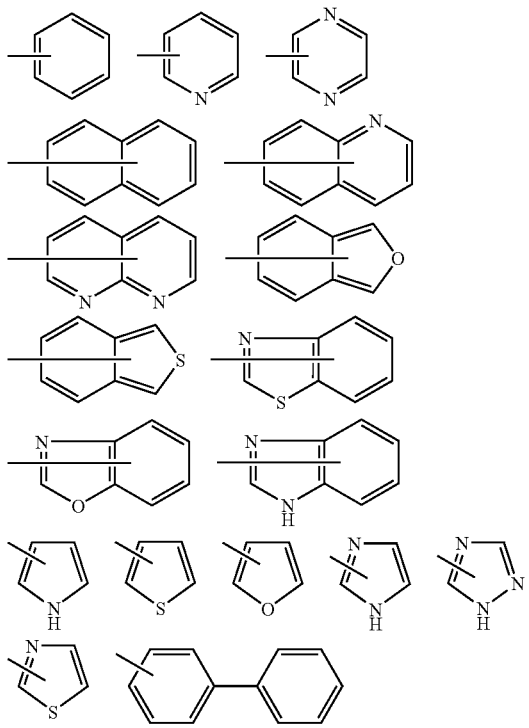

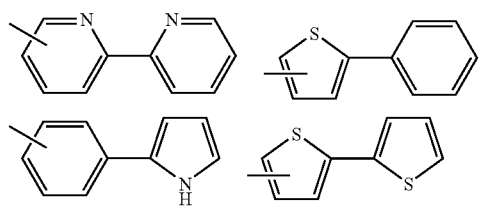

Preferable specific examples of $R^2$ and $R^5$ include the following formulae:

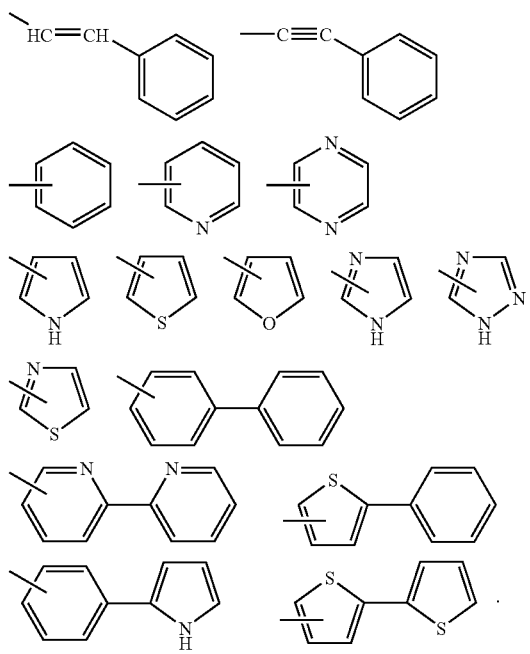

In accordance with the present invention, the ring opening quantum yield can be substantially decreased by introducing the above described Ar groups at $R^2$ and $R^5$, together with alkoxy groups introduced at $R^1$ and $R^4$.

$R^3$ and $R^6$ each represent independently, for example, a hydrogen atom; a linear or branched alkyl group with 1–10 carbon atoms such as methyl group, ethyl group, butyl group, and hexyl group; a linear or branched alkoxy group with 1–10 carbon atoms such as methoxy group, ethoxy group, butoxy group, and hexyloxy group; a halogen atom such as fluorine atom and chlorine atom; a linear or branched fluoroalkyl group with 1–6 carbon atoms such as trifluoromethyl group, pentafluoroethyl group, 2-fluoroethyl group, 2,2-difluoroethyl group, perfluoro-n-hexyl group, and 2-(perfluorobutyl) ethyl group; a cyano group; and an aryl group such as phenyl group and tosyl group which are optionally substituted. A relatively low-volumed group is preferable for $R^3$ and $R^6$, a linear alkyl group being especially preferable.

The examples of compounds belonging to the diheteroarylethene class in accordance with the present invention include the following formulae:

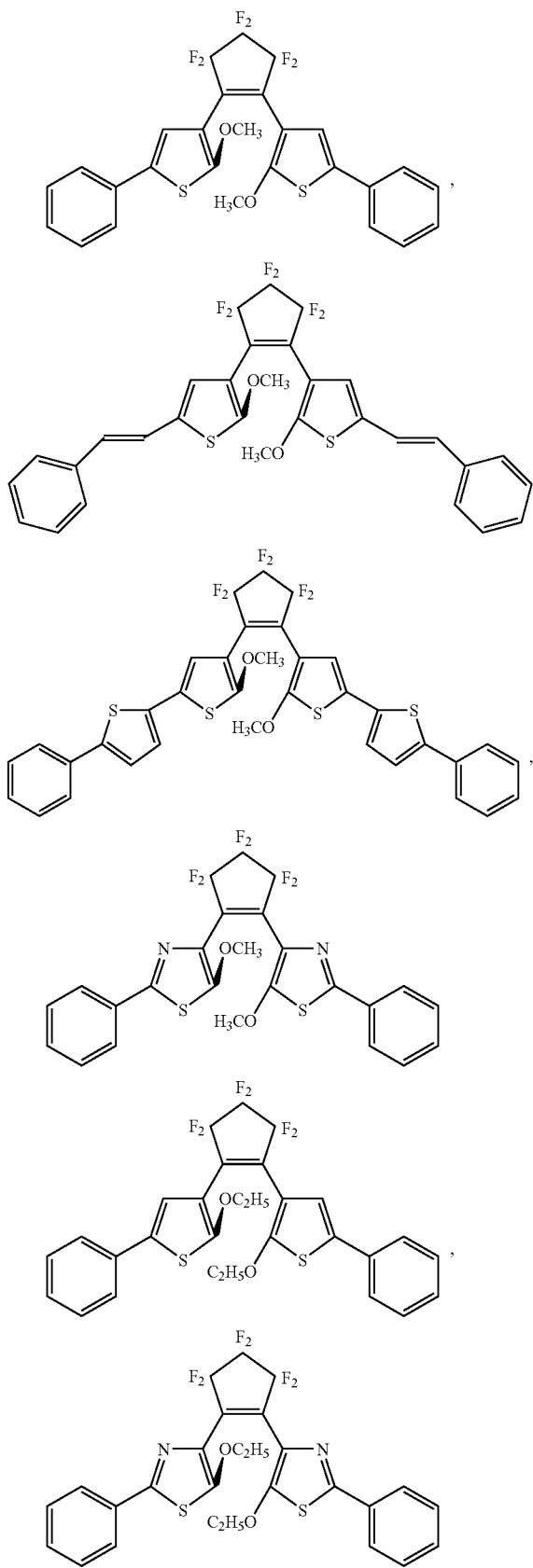

Each of the above compounds gives rise to ring closing reaction under irradiation of ultraviolet light, efficiently developing color which does not disappear in several hours in room environment, but can stand stably for a longer period of time.

Hereinafter, the present invention will be described more specifically by way of Synthesis Examples and Examples. However, the present invention is not limited to the following examples.

SYNTHESIS EXAMPLE 1

Synthesis of 1,2-bis[2-methoxy-5-phenyl-3-thienyl]perfluorocyclopentene (1-1) Synthesis of 3,5-dibromo-2-methoxythiophene

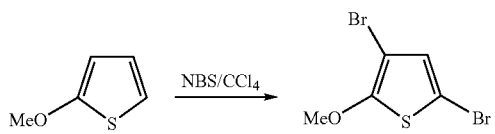

16 g (145 mmol) of 2-methoxythiophene was added into 40 ml of carbon tetrachloride. Then, 51 g (290 mmol) of N-bromosuccinimide and 250 ml of carbon tetrachloride were slowly added into it while being stirred in an ice water bath. After stirred overnight without the water bath, the solution was cooled again in an ice water bath and was filtered by suction filtration to eliminate solids. The filtrate was extracted using chloroform, was washed successively with a sodium bicarbonate aqueous solution and water, and was dried with addition of magnesium sulfate. The dried extract was condensed after removing magnesium sulfate by filtration. By developing the product with hexane on a silica gel column, a colorless liquid was obtained ($R_f$=0.65). Purification of the liquid by vacuum distillation (b.p.=90° C., 8 mmHg) gave the object compound, 3,5-dibromo-2-methoxythiophene. The yield was 24.6 g in weight and 62.3% in percentage.

$^1$H NMR (200 MHz, CDCl$_3$, TMS): ,,3.93 (s, 3H), 6.75 (s, 1H),

MSm/z=270, 272, 274 (M$^+$)

(1-2) Synthesis of 3-bromo-2-methoxy-5-phenylthiophene

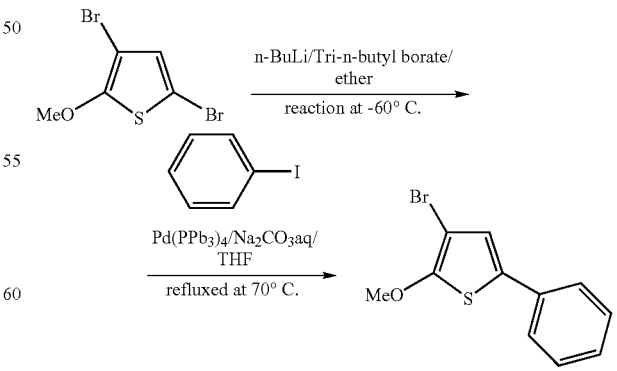

250 ml of anhydrous THF was added into 24 g (88 mmol) of 3,5-dibromo-2-methoxythiophene and was cooled to be −78° C. with dry ice-methanol. Then, 56 ml (92 mmol) of a solution containing 15% n-butyllithium hexane was slowly dripped into it. After being stirred for 1 hour, 32 ml (123 mmol) of tri-n-butyl borate was slowly dripped into it and stirred for 2 hours. After being returned to a room temperature, 90 ml of 20 wt % $Na_2CO_3$, 18 g (88 mmol) of iodobenzene, and 4.4 g (0.36 mmol) of $Pd(Ph_3P)_4$ were added to the solution and refluxed for 5 hours at 70° C. The reaction solution was extracted with ether, washed with a salt solution, and dried with addition of magnesium sulfate. The dried extract was condensed after removing magnesium sulfate by filtration. By developing the product with hexane on a silica gel column, a colorless solid 3-bromo-2-methoxy-5-phenylthiophene was obtained ($R_f$=0.35). The yield was 15 g in weight and 63% in percentage.

$^1$H NMR (400 MHz, $CDCl_3$, TMS): „4.00 (s, 3H), 6.98 (s, 1H), 7.2–7.5 (m, 5H)

MSm/z=268, 270 ($M^+$)

Anal. Calcd for $C_{11}H_9BrOS$: C=49.09, H=3.37. Found: C=49.20, H=3.38.

(1-3) Synthesis of 1,2-bis[2-methoxy-5-phenyl-3-thienyl] perfluorocyclopentene (compound 1)

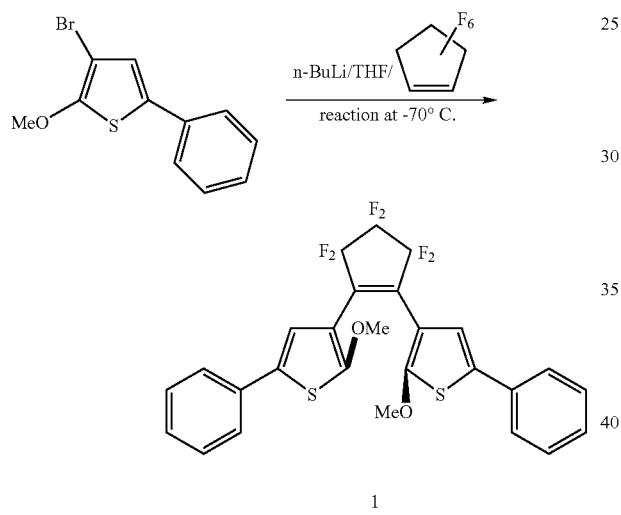

1

140 ml of anhydrous THF was added into 14 g (52 mmol) of 3-bromo-2-methoxy-5-phenylthiophene under argon atmosphere and was cooled to −60° C. or lower in dry ice-methanol bath. Then, 36 ml (52 mmol) of a solution containing 15% n-butyllithium hexane was slowly dripped into it and stirred for 1 hour. Then, 3.5 ml (26 mmol) of perfluorocyclopentene in 10 ml of anhydrous THF was slowly dripped into it at −60° C. or lower and was stirred for 2 hours. After being quenched by addition of methanol, the reaction solution was washed with 1N hydrochloric acid and was extracted with ether. The organic phase was washed with water, was dried with magnesium sulfate, and was condensed after magnesium sulfate was removed by filtration. By developing the product with hexane:chloroform=9:1 solvent on a silica gel column, the compound 1 was isolated ($R_f$=0.56). The yield was 7.2 g in weight and 50% in percentage.

$^1$H NMR (400 MHz, $CDCl_3$, TMS): „3.71 (s, 3H), 7.15 (s, 1H), 7.2–7.5 (m, 5H)

MSm/z=552 ($M^+$)

$^1$H NMR (200 MHz, $CDCl_3$, TMS): „3.71 (s, 6H), 7.16 (s, 2H), 7.2–7.5 (m, 10H)

Anal. Calcd for $C_{27}H_{18}F_6O_2S_2$: C=58.69, H=3.28. Found: C=58.87, H=3.37.

SYNTHESIS EXAMPLE 2

Synthesis of 1,2-bis[2-ethoxy-5-phenyl-3-thienyl] perfluorocyclopentene (2-1) Synthesis of 5-methoxy-2-phenylthiophene

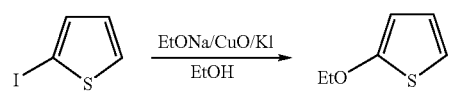

15 g (69 mmol) of 2-iodothiophene, 9.4 g (140 mmol) of sodium ethoxide, 2.7 g (35 mmol) of copper oxide, and 80 ml of anhydrous ethanol were added into a flask under argon atmosphere and were refluxed for two nights. Further, 7.0 g (100 mmol) of sodium ethoxide and 57 ml (0.35 mmol) of potassium iodide were added to it until material spots disappeared in TLC, and were refluxed for 7 hours. The reaction solution was returned to a room temperature, was filtered by suction filtration, and was mixed with ice water. The reaction solution was then extracted with ether, was washed with a salt solution, and was dried with magnesium sulfate. After filtering out the magnesium sulfate and evaporating the solvent, the product was subjected to vacuum distillation (b.p.=56° C., 8 mmHg) to give a colorless oil of 5-methoxy-2-phenylthiazole. The yield was 3.1 g in weight and 57% in percentage.

MSm/z=128 ($M^+$)

$^1$H NMR (200 MHz, $CDCl_3$, TMS): „1.41 (t, J=7 Hz, 3H), 4.09 (q, J=7 Hz, 2H), 6.20 (d, J=3.6 Hz, 1H), 6.53 (d, J=5.8 Hz, 1H), 6.71 (t, J=4.8 Hz, 1H)

(2-2) Synthesis of 3,5-dibromo-2-ethoxythiophene

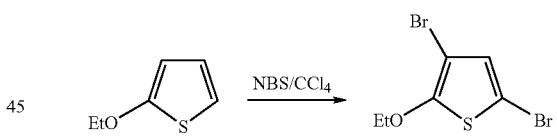

40 ml of carbon tetrachloride with 8.5 g (48 mmol) of N-bromosuccinimide was slowly added into 8 ml of carbon tetrachloride with 3.1 g (24 mmol) of 2-ethoxythiophene while being stirred in an ice water bath. Then, the ice water bath was removed and stirring was continued overnight. The reaction solution was cooled in an ice water bath and was filtered to remove solids by suction filtration. The reaction solution was then extracted with chloroform, was washed with sodium bicarbonate, sodium thiosulfate, and water, and was dried with magnesium sulfate. After filtering out the magnesium sulfate and evaporating the solvent, the product was developed with hexane on a silica column to give thin yellow oil of 3,5-dibromo-2-ethoxythiophene ($R_f$=0.48). The yield was 6.5 g in weight and 94% in percentage.

MSm/z=284, 286, 288 ($M^+$)

$^1$H NMR (200 MHz, $CDCl_3$, TMS): „1.43 (t, J=7 Hz, 3H), 4.13 (q, J=7 Hz, 2H), 6.75 (s, 1H),

Anal. Calcd for $C_6H_6Br_2OS$: C=25.20, H=2.11. Found: C=25.50, H=2.14.

(2-3) Synthesis of 3-bromo-2-ethoxy-5-phenylthiophene

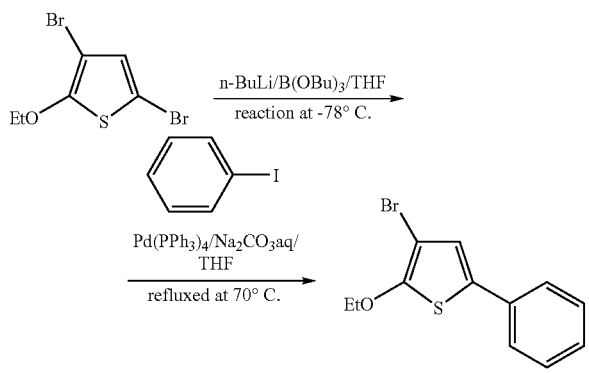

150 ml of anhydrous THF and 6.5 g (23 mmol) of 3,5-dibromo-2-ethoxythiophene was added into a flask under argon atmosphere. Then, 15 ml (25 mmol) of a solution containing 15% n-butyllithium hexane was slowly dripped into it at −78° C. After being stirred for 1 hour at −78° C., 9.1 ml (34 mmol) of tri-n-butyl borate was slowly dripped into it and was stirred for 1.5 hours. After being returned to a room temperature and quenched with water, 4.6 g (23 mmol) of iodobenzene, 1.1 g (0.95 mmol) of Pd(PPh$_3$)$_4$, and 50 ml of 20 wt % Na$_2$CO$_3$ aqueous solution was added to the solution and was refluxed overnight at 70° C. The reaction solution was extracted with ether, was washed with a salt solution, and was dried with magnesium sulfate. After filtering out the magnesium sulfate and evaporating the solvent, the product was developed with hexane on a silica column to give 3-bromo-2-ethoxy-5-phenylthiophene (R$_f$=0.31). The yield was 4.9 g in weight and 76% in percentage.

MSm/z=282, 284 (M$^+$)

$^1$H NMR (200 MHz, CDCl$_3$): ,,1.48 (t, J=7 Hz, 3H), 4.21 (q, J=7 Hz, 2H), 6.98 (s, 1H), 7.25–7.49 (m, 5H),

Anal. Calcd for C$_{12}$H$_{11}$BrOS: C=50.90, H=3.92. Found: C=51.17, H=3.89.

(2-4) Synthesis of 1,2-bis[2-ethoxy-5-phenyl-3-thienyl]perfluorocyclopentene (compound 2)

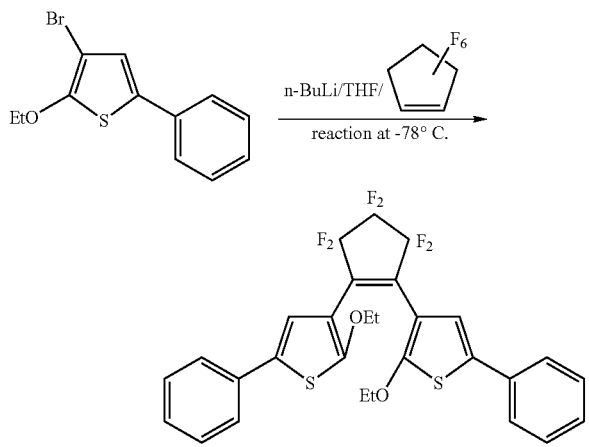

4.9 g (17 mmol) of 3-bromo-2-ethoxy-5-phenylthiophene and 45 ml of anhydrous THF was added into a flask under argon atmosphere. Then, 12 ml (19 mmol) of a solution containing 15% n-butyllithium hexane was slowly dripped into it at −78° C. After being stirred for 1.5 hours at −78° C., 5 ml of anhydrous THF with 1.2 ml (34 mmol) of perfluorocyclopentene was slowly dripped into it and was stirred for 3 hours. After being returned to the room temperature and being quenched with water, the reaction solution was washed with 1N hydrochloric acid. The reaction solution was extracted with ether, was washed with a salt solution, and was dried with magnesium sulfate. After filtering out the magnesium sulfate, the product was developed with hexane: chloroform=7:3 solvent on a silica gel column to isolate 1,2-bis[2-ethoxy-5-phenyl-3-thienyl]perfluorocyclopentene that is the compound 2. The yield was 1.8 g in weight and 36% in percentage.

MSm/z=580 (M$^+$)

$^1$H NMR (200 MHz, CDCl$_3$): ,,1.08 (t, J=7 Hz, 6H), 3.92 (q, J=7 Hz, 4H), 7.22 (s, 2H), 7.26–7.51 (m, 10H),

Anal. Calcd for C$_{29}$H$_{22}$N$_2$F$_6$O$_2$S$_2$: C=59.99, H=3.82. Found: C=60.03, H=3.80.

SYNTHESIS EXAMPLE 3

Synthesis of 1,2-bis[5-methoxy-2-phenyl-3-thiazoyl]perfluorocyclopentene (3-1) Synthesis of 5-methoxy-2-phenylthiazole

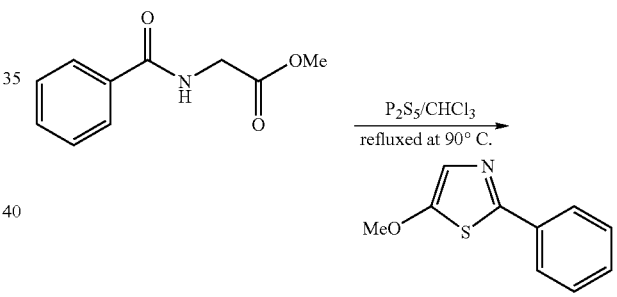

1.0 g (5.2 mmol) of benzoylglycin methyl ester and 1.4 g (6.4 mmol) of diphosphorous pentasulfide was added quickly into a reaction vessel. After that, anhydrous chloroform (15 ml) was also added and heated to around 80° C. When decrease in hydrogen sulfide generation and white precipitate formation in the reaction solution were observed, an argon balloon was attached and the solution was refluxed for 24 hours. After completion of reaction, the precipitate was dissolved by adding an aqueous solution of strong alkali to the solution, and the organic phase was extracted with dichloromethane, followed by drying with addition of magnesium sulfate and removal of solvent. The product was developed with ethyl acetate:hexane=5:5 solvent on a silica column to give 5-methoxy-2-phenylthiazole (R$_f$=0.40). The yield was 566 mg in weight and 57% in percentage.

MSm/z=191 (M$^+$)

$^1$H NMR (200 MHz, CDCl$_3$): ,,7.84–7.80 (m, 2H), 7.60–7.40 (m, 3H), 6.65 (br s, 1H), 4.27 (d, J=4.8 Hz, 2H), 3.82 (s, 3H),

Anal. Calcd for C$_{10}$H$_9$NOS: C=62.80, H=4.74, N=7.32. Found: C=62.64, H=4.78, N=7.34.

(3-2) Synthesis of 4-bromo-5-methoxy-2-phenylthiazole

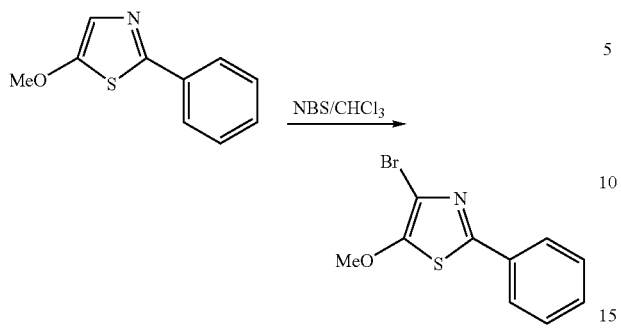

400 mg (2.1 mmol) of N-bromosuccinimide was added into 10 ml of anhydrous chloroform with 400 mg (2.1 mmol) of 5-methoxy-2-phenylthiazole under 0° C. condition and was stirred for 4 hours at a room temperature. After completion of reaction, the organic phase was extracted with ethyl acetate, and was dried with addition of magnesium sulfate. After removing the solvent, the product was developed with ethyl acetate:hexane=1:3 solvent on silica column to give 4-bromo-5-methoxy-2-phenylthiazole ($R_f$=0.50). The yield was 550 mg in weight and 97% in percentage.

MS m/z=271 (M$^+$)

$^1$H NMR (200 MHz, CDCl$_3$, TMS): „7.85–7.78 (m, 2H), 7.45–7.36 (m, 3H), 4.03 (s, 3H),

Anal. Calcd for C$_{10}$H$_8$NOSBr: C=44.46, H=2.98, N=5.18. Found: C=44.56, H=2.99, N=5.19.

(3-3) Synthesis of 1-[5-methoxy-2-phenyl-3-thiazoil]perfluorocyclopentene

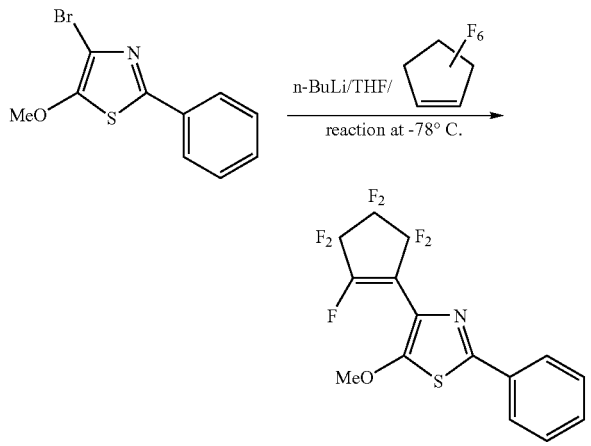

8 ml of anhydrous THF was added into 540 mg (2.0 mmol) of 4-bromo-5-methoxy-2-phenylthiazole under argon atmosphere and was cooled to −78° C. or lower with a methanol solution of dry ice. 1.3 ml (2.1 mmol) of a solution containing 15% n-butylithium hexane was dripped slowly into it and was stirred for 15 minutes. Then, 0.2 ml (0.93 mmol) of perfluorocyclopentene was added in 2 ml of anhydrous THF, was slowly dripped into it at −78° C. or lower, and was stirred for 2.5 hours. After being quenched by addition of water, the reaction solution was extracted with ether. The organic phase was washed with water and was dried with magnesium sulfate, was filtered to remove the magnesium sulfate, and was concentrated. The product was developed with hexane:ethyl acetate=1:3 solvent on a silica gel column to isolate 1-[5-methoxy-2-phenyl-3-thiazoil]perfluorocyclopentene ($R_f$=0.30). The yield was 510 mg in weight and 72% in percentage.

MS m/z=383 (M$^+$)

$^1$H NMR (200 MHz, CDCl$_3$, TMS): „7.88–7.80 (m, 2H), 7.48–7.40 (m, 3H), 4.13 (s, 3H),

Anal. Calcd for C$_{15}$H$_8$NOSF$_7$: C=47.00, H=2.10, N=3.65. Found: C=47.25, H=2.08, N=3.66.

(3-4) Synthesis of 1,2-bis[5-methoxy-2-phenyl-3-thiazoyl]perfluorocyclopentene (compound 3)

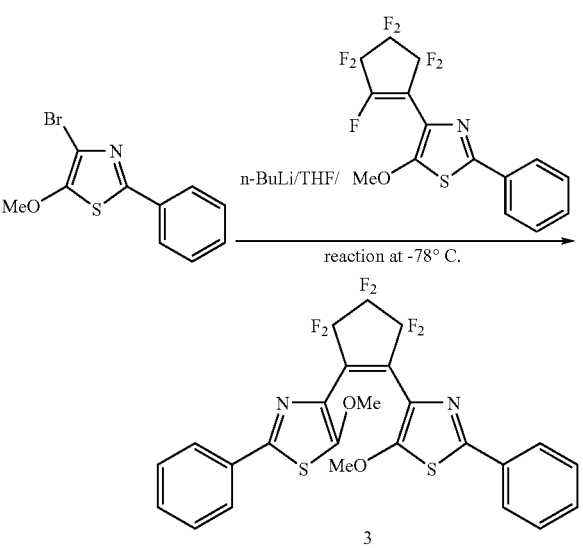

8 ml of anhydrous THF was added into 540 mg (2.0 mmol) of 4-bromo-5-methoxy-2-phenylthiazole under argon atmosphere and was cooled to −78° C. or lower with a methanol solution of dry ice. 1.3 ml (2.1 mmol) of a solution containing 15% n-butylithium hexane was dripped slowly into it and was stirring for 15 minutes. Then, 510 mg (1.33 mmol) of 1-[5-methoxy-2-phenyl-3-thiazoil]perfluorocyclopentene was added into 2 ml of anhydrous THF, was slowly dripped into it at −78° C. or lower, and was stirred for 2.5 hours. After quenching by addition of water, the solution was extracted with ether. The organic phase was washed with water, was dried with magnesium sulfate, was filtered to remove the magnesium sulfate, and was concentrated. The product was developed with hexane:ethyl acetate=3:7 solvent on a silica gel column to isolate 1,2-bis[5-methoxy-2-phenyl-3-thiazoil]perfluorocyclopentene that is the compound 3 ($R_f$=0.10). The yield was 540 mg in weight and 68% in percentage.

MS m/z=554 (M$^+$)

$^1$H NMR (200 MHz, CDCl$_3$, TMS): „7.86–7.74 (m, 4H), 7.44–7.35 (m, 6H), 3.83 (s, 6H),

Anal. Calcd for C$_{25}$H$_{16}$N$_2$O$_2$S$_2$F$_6$: C=54.15, H=2.91, N=5.05. Found: C=54.25, H=2.97, N=5.10.

EXAMPLE 1

The compound 1 synthesized in Synthesis Example 1 was dissolved in hexane. This solution was irradiated with light of 313 nm. The solution developed blue color of which absorption maximum was observed at 625 nm („=1.5×10$^4$ M$^{-1}$ cm$^{-1}$). The generation quantum yield of the colored substance (in the closed-ring form) was determined to be 0.44. The blue color showed no remarkable fading even when irradiated with visible light. The ring opening quantum yield corresponding to fading was determined to be $1.7 \times 10^{-5}$.

(Measuring Procedure for Ring Closing Quantum Yield)

(1) Hexane solutions in the open-ring forms of the compound 1 and of 1,2-bis(2-methyl-5-phenyl-3-thienyl)perfluorocyclopentene (the compound 2) as a comparative sample were prepared. The both solutions were adjusted to make their absorbance at irradiation wavelength of 309 nm (absorption maximum wavelength of the compound 1 in the open-ring form) to be the same level within a range from 0.2 to 0.3.

(2) The solution volumes in absorption cells were equalized.

(3) In measurement, the absorbance changes of the closed form compounds at absorption maximum wavelength in visible light region (the compound 1: 625 nm, the compound 2: 575 nm) were detected. The compound 1 and the compound 2 as a comparative sample were irradiated with light of 309 nm using a xenon lamp, and measurements were made for 10 points in absorbance range of detected wavelength of about 0–0.1.

(4) The absorbance changes relative to time were plotted, and, from comparison of inclinations for the both compounds, a ring closing quantum yield of 0.44 was obtained for the compound 1 (the quantum yield of the compound 2 was 0.59).

A quantitative measurement of fading tendency was conducted as follows. The fading by light was hardly observed.

(Measuring Procedure for Ring Opening Quantum Yield)

(1) A hexane solution of the compound 1 was prepared and was irradiated with ultraviolet light (wavelength 313 nm) to adjust its absorbance at a wavelength of 625 nm, which is the absorption maximum wavelength in visible light region, to be about 0.5. The hexane solution was irradiated with a light of 625 nm using a xenon lamp and was measured for every time period for which the absorbance may be changed by about 0.01.

(2) Fulgide was used as a comparative sample. A toluene solution of the fulgide was prepared and was irradiated with light of 492 nm. The absorbance at a wavelength 492 nm was measured at several points in the approximate changing range of from 0.5 to 0.2, similarly to the case of the compound 1.

(3) Using an actinometer, the light quantities at wavelengths of 692 nm and of 492 nm were measured.

(4) Values of $\log(10^A - 1)$ (wherein A represents absorbance) were plotted against time. From the inclination of the plotting which was corrected using the values of light quantities obtained in (3), the relative quantum yield was determined. As a result, the quantum yield of fading reaction (ring opening reaction) was determined to be $1.7 \times 10^{-5}$. Even when the solution was exposed to ambient light for three months, no fading (ring opening reaction) was observed.

EXAMPLE 2

The compound 1 (10 mg) synthesized in Synthesis Example 1 and 200 mg of polystyrene were dissolved in 3 mL of toluene, and the solution was cast on a Teflon plate to form a polystyrene film having a thickness of 500 ,,m. Irradiation of light of 366 nm onto the film instantly colored the film in blue color. This blue color showed no fading (ring opening reaction) even when exposed to ambient light for three months.

EXAMPLE 3

The compound 2 synthesized in Synthesis Example 2 was dissolved in toluene, and the solution was irradiated with light of 313 nm. The solution developed blue color of which absorption maximum was observed at 625 nm (,,=$1.3 \times 10^4$ $M^{-1}$ $cm^{-1}$). The generation quantum yield of the colored substance (in the closed form) was determined to be 0.48. The blue color showed no remarkable fading even when irradiated with visible light. The ring opening quantum yield corresponding to fading was determined to be $2.5 \times 10^{-4}$.

(Measuring Procedure for Ring Closing Quantum Yield)

(1) Hexane solutions in the open-ring forms of the compound 2 and of fulgide as a comparative sample were prepared. The both solutions were adjusted to make their absorbance at irradiation wavelength of 310 nm (absorption maximum wavelength of the compound 3 in the open-ring form) to be the same level within a range from 0.2 to 0.3.

(2) The solution volumes in absorption cells were equalized.

(3) In measurement, the absorbance changes of closed form compounds at absorption maximum wavelength in visible light region (the compound 2: 625 nm, the fulgide: 492 nm) were detected. The compound 2 and the fulgide were both irradiated with light of 310 nm using a xenon lamp, and measurements were made for 10 points in absorbance range of detected wavelength of from about 0 to about 0.1.

(4) The absorbance changes relative to time were plotted and, from comparison of inclinations for both compounds, a ring closing quantum yield of 0.48 was obtained for the compound 2 (the quantum yield of fulgide was 0.20).

A quantitative measurement of fading tendency was conducted as follows. The fading by light was hardly observed.

(Measuring Procedure for Ring Opening Quantum Yield)

(1) A hexane solution of the compound 2 was prepared and was irradiated with ultraviolet light (wavelength 313 nm) to adjust its absorbance at a wavelength of 625 nm, which is the absorption maximum wavelength in visible light region, to be about 0.4. The hexane solution was irradiated with a light of 625 nm using a xenon lamp and was measured for every time period for which the absorbance may be changed by about 0.01.

(2) Fulgide was used as a comparative sample. A toluene solution of the fulgide was prepared and was irradiated with light of 492 nm. The absorbance at a wavelength 492 nm was measured at several points in the approximate changing range of from 0.4 to 0.2, similarly to the case of the compound 2.

(3) Using an actinometer, the light quantities at wavelengths of 625 nm and of 492 nm were measured.

(4) Values of $\log(10^A - 1)$ (wherein A represents absorbance) were plotted against time. From the inclination of the plotting which was corrected using the values of light quantities obtained in (3), the relative quantum yield was determined. As a result, the quantum yield of fading reaction (ring opening reaction) was determined to be $2.5 \times 10^{-4}$.

EXAMPLE 4

The compound 3 synthesized in Synthesis Example 3 was dissolved in toluene, and the solution was irradiated with light of 313 nm. The solution developed violet color of which absorption maximum was observed at 555 nm ($\varepsilon=1.3\times10^4$ M$^{-1}$ cm$^{-1}$). The generation quantum yield of the colored substance (in the closed-ring form) was determined to be 0.29. The violet color showed no remarkable fading even when irradiated with visible light. The ring opening quantum yield corresponding to fading was determined to be $3.3\times10^{-4}$.

(Measuring Procedure for Ring Closing Quantum Yield)

(1) Toluene solutions in the open-ring forms of the compound 3 and of fulgide as a comparative sample were prepared. The absorbance of the both solutions at irradiation wavelength of 313 nm were adjusted to a same level within a range from 0.2 to 0.3.

(2) The solution volumes in absorption cells were equalized.

(3) In measurement, the absorbance changes of closed form compounds at absorption maximum wavelength in visible light region (compound 3: 555 nm, fulgide: 492 nm) were detected. The compound 3 and the fulgide were both irradiated with light of 313 nm using a xenon lamp, and measurements were made for 10 points in absorbance range of detected wavelength of from about 0 to about 0.1.

(4) The absorbance changes relative to time were plotted and, from comparison of inclinations for both compounds, a ring closing quantum yield of 0.29 was obtained for the compound 3 (the quantum yield of fulgide was 0.20).

A quantitative measurement of fading tendency was conducted as follows. The fading by light was hardly observed.

(Measuring Procedure for Ring Opening Quantum Yield)

(1) A toluene solution of the compound 3 was prepared and was irradiated with ultraviolet light (wavelength 313 nm) to adjust its absorbance at a wavelength of 555 nm, which is the absorption maximum wavelength in visible light region, to be about 0.4. The hexane solution was irradiated with a light of 555 nm using a xenon lamp and was measured for every time period for which the absorbance may be changed by about 0.01.

(2) Fulgide was used as a comparative sample. A toluene solution of the fulgide was prepared and was irradiated with light of 492 nm. The absorbance at a wavelength 492 nm was measured at several points in the approximate changing range of from 0.4 to 0.2, similarly to the case of the compound 3.

(3) Using an actinometer, the light quantities at wavelengths of 555 nm and of 492 nm were measured.

(4) Values of $\log(10^A-1)$ (wherein A represents absorbance) were plotted against time. From the inclination of the plotting which was corrected using the values of light quantities obtained in (3), the relative quantum yield was determined. As a result, the quantum yield of fading reaction (ring opening reaction) was determined to be $3.3\times10^{-4}$.

INDUSTRIAL APPLICABILITY

As described in detail hereinabove, according to the present invention, a photochromic material is provided which has a substantially low ring opening quantum yield, practically no fading problem under ambient light, and an excellent long-time stability of recorded or displayed information.

The photochromic material of the present invention has possible applications not only for the production of optical memory media and optical display materials, but also to novel optical elements.

What is claimed is:

1. A photochromic material comprising a compound having a ring opening quantum yield of $10^{-3}$ or lower, which is a diheteroarylethene, represented by the following formula (I):

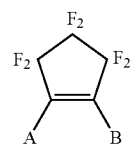

(I)

wherein, in the formula (I), A represents following substituents (i) or (ii), and B represents following substituents (iii) or (iv);

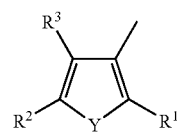

(i)

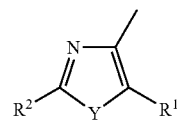

(ii)

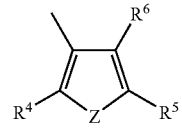

(iii)

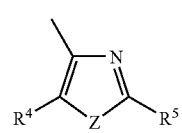

(iv)

wherein, in the substituents (i) and (ii), R$^1$ represents an alkoxy group, R$^2$ represents -Q-Ar, Q represents a direct bond or a divalent group and Ar represents an aromatic hydrocarbon ring or an aromatic heterocycle which are optionally substituted, R$^3$ represents a hydrogen atom, an alkyl group, an alkoxy group, a halogen atom, a fluoroalkyl group; a cyano group, or an aryl group which is optionally substituted, and Y represents —O— or —S—; and in the substituents (iii) and (iv), R$^4$ represents an alkoxy group, R$^5$ represents -Q-Ar, Q represents a direct bond or a divalent group and Ar represents an aromatic hydrocarbon ring or an aromatic heterocycle which are optionally substituted, R$^6$ represents a hydrogen atom, an alkyl group, an alkoxy group, a halogen atom, a fluoroalkyl group, a cyano group, or an aryl group which is optionally substituted, and Z represents —O— or —S—.

2. A photochromic material as claimed in claim 1, wherein the ring opening quantum yield is $3.3\times10^{-4}$ or lower.

3. A photochromic material as claimed in claim 1, wherein R$^1$ and R$^4$ in the substituents (i)–(iv) of said formula (I) each comprises independently an alkoxy group having 1–3 carbon atoms.

4. A photochromic material as claimed in claim 3, wherein $R^1$ and $R^4$ each comprises a methoxy group.

5. A photochromic material as claimed in claim 1, wherein Q in Q-Ar corresponding to $R^2$ and $R^5$ in the substituents (i)–(iv) of said formula (I) each comprises independently a direct bond, $-(-CH=CH-)n-$ (wherein n=1–5), or $-(C\equiv C-)n-$ (wherein n=1–5), whereby Ar comprises a single 5- or 6-member ring, or two or three 5- or 6-member rings directly bonded or condensed, each of said rings being optionally substituted.

6. A photochromic material as claimed in claim 5, wherein Ar in Q-Ar corresponding to $R^2$ and $R^5$ is selected independently from the group consisting of the following formulae:

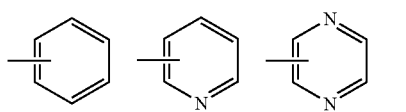
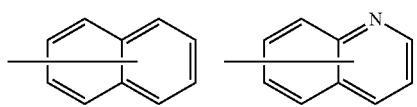
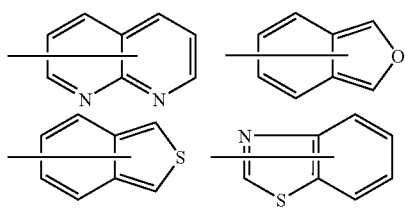
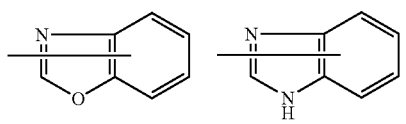
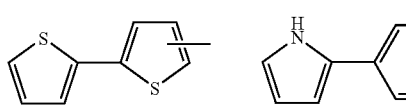
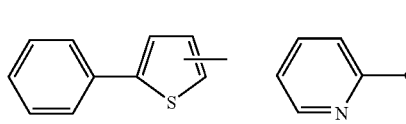
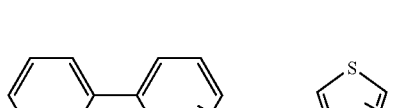
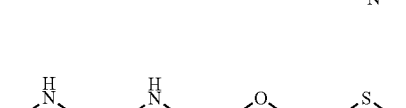
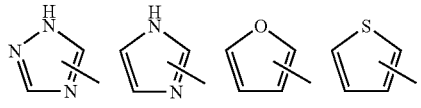

7. A photochromic material as claimed in claim 6, wherein $R^2$ and $R^5$ are each selected independently from the group consisting of following formulae:

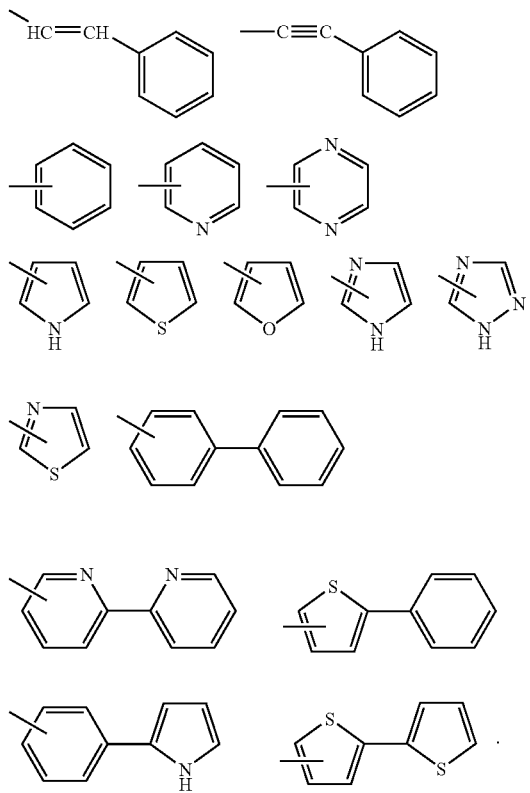

8. A photochromic material as claimed in claim 1, wherein $R^3$ and $R^6$ each comprises independently a linear alkyl group.

9. A photochromic material as claimed in claim 1, wherein the photochromic material comprises a compound, which is a diheteroarylethene, selected from the group consisting of following formulae:

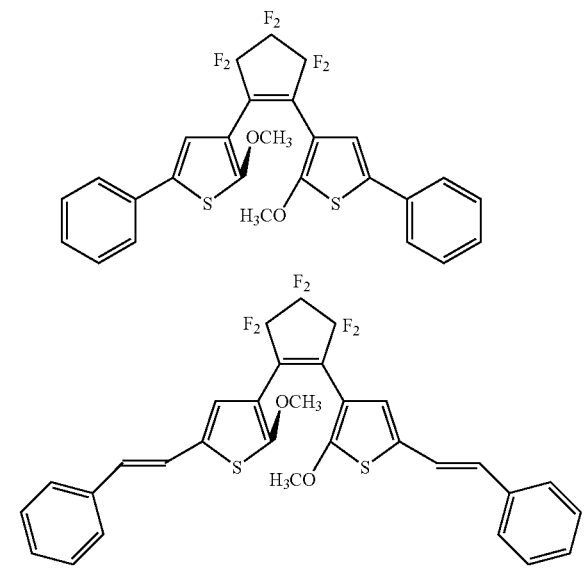

-continued
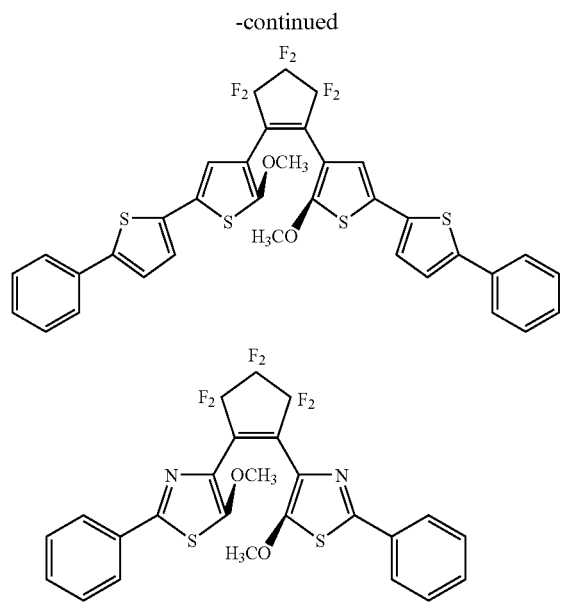
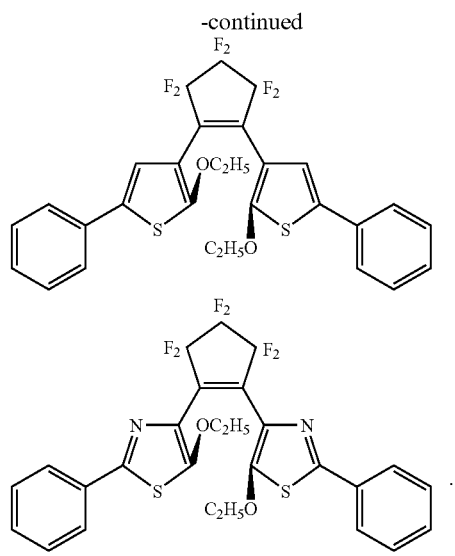
* * * * *